US010667677B2

(12) United States Patent
Dresher et al.

(10) Patent No.: US 10,667,677 B2
(45) Date of Patent: *Jun. 2, 2020

(54) MEDICAL DEVICE VISUALIZATION SYSTEM

(71) Applicant: Boston Scientific Scimed, Inc., Maple Grove, MN (US)

(72) Inventors: Russell Dresher, Hudson, MA (US); Andrew Calabrese, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/794,502

(22) Filed: Oct. 26, 2017

(65) Prior Publication Data

US 2018/0042469 A1 Feb. 15, 2018

Related U.S. Application Data

(63) Continuation of application No. 13/886,009, filed on May 2, 2013, now Pat. No. 9,826,892.

(60) Provisional application No. 61/659,258, filed on Jun. 13, 2012.

(51) Int. Cl.
*A61B 1/06* (2006.01)
*A61B 1/04* (2006.01)
*A61B 1/00* (2006.01)

(52) U.S. Cl.
CPC ............ *A61B 1/06* (2013.01); *A61B 1/00096* (2013.01); *A61B 1/00165* (2013.01); *A61B 1/04* (2013.01); *A61B 1/0676* (2013.01); *A61B 1/0684* (2013.01)

(58) Field of Classification Search
CPC ... A61B 1/06; A61B 1/00096; A61B 1/00165; A61B 1/04; A61B 1/0676; A61B 1/0684
See application file for complete search history.

(56) References Cited

U.S. PATENT DOCUMENTS

| 6,736,776 B2 | 5/2004 | Wendlandt et al. |
| 2012/0310047 A1* | 12/2012 | Kasamatsu .......... A61B 1/0638 600/178 |
| 2013/0190561 A1* | 7/2013 | Oskin ................ A61B 1/00064 600/104 |

FOREIGN PATENT DOCUMENTS

| WO | WO 93/25155 A1 | 12/1993 |
| WO | WO 94/17434 A1 | 8/1994 |

* cited by examiner

*Primary Examiner* — Timothy J Neal
*Assistant Examiner* — William B Chou
(74) *Attorney, Agent, or Firm* — Bookoff McAndrews, PLLC

(57) ABSTRACT

Embodiments of the disclosure may include a medical device comprising an elongate member including a proximal region and a distal region. The elongate member can further include a handle at the proximal region and a tip at the distal region. The tip can include one or more openings, wherein one of the one or more openings at least partially houses an illumination unit. The illumination unit may further comprise a light source, a near-field diffuser proximate to the light source, and a far-field aperture proximate to the light source.

20 Claims, 4 Drawing Sheets

MEDICAL DEVICE VISUALIZATION SYSTEM

CROSS-REFERENCE TO RELATED APPLICATIONS

This application is a continuation of U.S. application Ser. No. 13/886,009, filed May 2, 2013, now U.S. Pat. No. 9,826,892, which claims the benefit of priority from U.S. Provisional Application No. 61/659,258, filed on Jun. 13, 2012, all of which are incorporated herein by reference in their entireties.

FIELD OF THE DISCLOSURE

Embodiments of the present disclosure include medical devices, and more particularly, medical devices including enhanced visualization and methods of use.

BACKGROUND OF THE DISCLOSURE

Adequate visualization has posed a challenge in the exploration and treatment of internal areas of the human body. Visualization may be especially troublesome in minimally invasive procedures in which small diameter, elongate instruments, such as catheters or endoscopes, may be navigated through natural passageways and cavities of a patient to a region of interest (work site).

In conventional minimally invasive procedures, an endoscope or catheter may be inserted into the body for diagnostic or therapeutic purposes. A distal end of an endoscope may be inserted into the body through an opening in the body. This opening may be a natural anatomic opening, such as, for example, the mouth, rectum, vagina, etc., or an incision made on the body. The endoscope may be pushed into the body such that the distal end of the endoscope proceeds from the point of insertion to a work site within the body by traversing a body lumen, for example, the gastric, pulmonary, esophageal, or urological tracts.

Once inside the body, performing diagnostic and treatment procedures requires sufficiently clear visualization. Navigating and identifying regions of interest may require down-lumen visualization. For down-lumen visualization, high-intensity light with a small spot size may be directed towards the center of a body lumen. When directed towards near-field objects, however, this light may become saturating and image details may be lost. By contrast, visualizing the near-field lumen periphery may require wide-angle, low-intensity light. While such low-intensity light avoids saturation of near-field objects, it may not provide enough illumination to visualize down lumen. These variations in illumination requirements may make navigation and visualization of the work site difficult, potentially increasing procedure time and decreasing accuracy, and thus increasing the possibility of complications for the patient.

Conventional endoscopes may utilize complex and/or expensive systems, such as arrays of optical fibers or light-emitting diodes ("LEDs") at a distal region of an endoscope in order to provide uniform illumination in both the near and far fields. But such devices may increase the size of endoscopes, making them cumbersome to maneuver and restricting the cavities through which they may pass. Additionally, they may increase the cost of manufacturing and maintaining these instruments.

Accordingly, a need exists for a compact, cost-effective visualization unit capable of achieving adequate uniform far-field and near-field illumination. The medical devices and related methods of the present disclosure are directed to improvements in the existing technology and overcome at least some of the deficiencies in the prior art.

SUMMARY OF THE DISCLOSURE

Various embodiments of the disclosure may include one or more of the following aspects.

In accordance with one embodiment, a medical device may comprise an elongate member including a proximal region and a distal region. The elongate member can further include a handle at the proximal region and a tip at the distal region. The tip can include one or more openings, wherein one of the one or more openings at least partially houses an illumination unit. The illumination unit may further comprise a light source, a near-field diffuser proximate to the light source, and a far-field aperture proximate to the light source.

In accordance with another embodiment, a medical device may comprise an elongate member including a proximal region and a distal region and one or more channels extending from the proximal region to the distal region. A channel of the one or more channels may be configured to carry light or a light signal to a distal region of the elongate member. The light or light signal may be from only one optical fiber or only one light emitting diode. Additionally, the medical device can include a near-field diffuser at the distal region of the elongate member configured to provide near-field illumination. The medical device can also include a far-field aperture at the distal region of the elongate member configured to provide far-field illumination. The medical device may also include an imaging unit.

In this respect, before explaining multiple embodiments of the present disclosure in detail, it is to be understood that the present disclosure is not limited in its application to the details of construction and to the arrangements of the components set forth in the following description or illustrated in the drawings. The present disclosure is capable of embodiments in addition to those described and of being practiced and carried out in various ways. Also, it is to be understood that the phraseology and terminology employed herein, as well as in the abstract, are for the purpose of description and should not be regarded as limiting.

The accompanying drawings illustrate certain exemplary embodiments of the present disclosure and, together with the description, serve to explain the principles of the present disclosure. As such, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

DETAILED DESCRIPTION

Reference will now be made in detail to exemplary embodiments of the invention, examples of which are illustrated in the accompanying drawings. Wherever possible, the same reference numbers will be used throughout the drawings to refer to the same or like parts. Also, any aspect set forth in any embodiment may be used with any other embodiment set forth herein.

The terms "proximal" and "distal" are used herein to refer to the relative positions of the components of an exemplary medical device. When used herein, "proximal" refers to a position relatively closer to the exterior of the body or closer to the physician, or other user, using the medical device. In contrast, "distal" refers to a position relatively further away from the user using the medical device or closer to the interior of the body.

While the described systems and methods may generally refer to medical devices and procedures, the described systems and their methods of use are not limited to any particular medical diagnostic or treatment procedure. Moreover, the systems and devices described herein can perform nonmedical applications, such as the inspection or repair of machinery.

Figure 1:
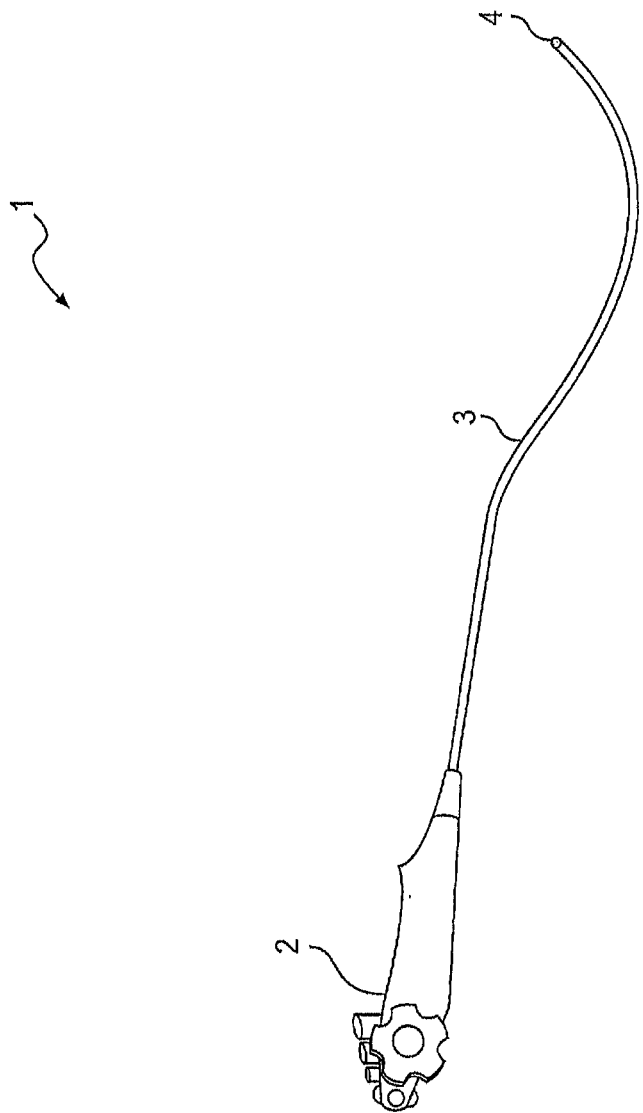
FIG. 1 illustrates a medical device, according to an exemplary disclosed embodiment.

FIG. 1 illustrates a medical device 1 according to an exemplary embodiment. Medical device 1 may include any device configured to allow an operator to access and view internal body anatomies of a patient. Such devices include, for instance, an endoscope, a catheter, a guide tube, or the like. Medical device 1 may be configured for insertion into a variety of body lumens and/or cavities, such as, for example, any portion of a urinary tract including a ureter, a gastrointestinal lumen including an esophagus, a biliary duct, pancreatic duct, a vascular lumen, an airway, and the like. Medical device 1 also may be used, for example, in natural orifice transluminal endoscopic surgery (NOTES) procedures or single incision laparoscopic surgical (SILS) procedures. Accordingly, medical device 1 can be shaped and sized for placement into a patient via a body cavity or an incision. For purposes of the present disclosure, medical device 1 may include a single-use, disposable endoscope, or medical device 1 may include a reusable endoscope.

Medical device 1 may include an elongate member 3 having a proximal end and a distal end. A handle assembly 2 may be operably connected to a proximal region of elongate member 3 and configured for steering and/or controlling a distal region of medical device 1. Medical device 1 may be used alone or as part of a larger surgical system (not shown). Examples of such surgical systems are described in U.S. Pat. No. 6,736,773, and U.S. Patent Publication Nos. 2011/0213206 and 2008/0188868, all of which are incorporated herein in their entirety by reference. A distal tip 4 may be operably connected to a distal region of elongate member 3 and configured for positioning at a work site in a body cavity. Elongate member 3 may be flexible, or may include one or more portions that are flexible, to allow elongate member 3 to be maneuvered within the body and to traverse tortuous anatomical lumens. For instance, elongate member 3 may be uniformly flexible or may include a plurality of portions having varying degrees of flexibility or rigidity. In some embodiments, elongate member 3 may be rigid, or may include one or more portions that are rigid.

Elongate member 3 may be formed of any suitable material, for instance, rubber, silicon, plastic, stainless steel, metal-polymer composites, and metal alloys. In some embodiments, elongate member 3 may include layers of different materials and reinforcements. Elongate member 3 may have any cross-sectional shape and/or configuration and may be any desired dimension that can be received in a body cavity. In some embodiments, elongate member 3 may be made of, or coated with, a polymeric or lubricious material to enable medical device 1 to more easily pass through a body cavity.

Elongate member 3 can further include one or more channels 15, 16 (shown in FIG. 2B) extending through elongate member 3 and/or handle assembly 2 and/or distal tip 4. Channels 15, 16 may have any size, cross-sectional area, shape, and/or configuration. Medical device 1 and channels 15, 16 may be configured to deliver instruments, such as forceps, graspers, baskets, snares, probes, scissors, retrieval devices, needles, and the like, into a patient's body. In some embodiments, channels 15, 16 could include an irrigation channel for a suitable fluid, such as water or saline, and/or an insufflation channel for insufflation gas. Accordingly, channels 15, 16 may be coupled to a fluid or gas source at a proximal region (not shown). The irrigation and/or insufflation channels can be used, for example, to irrigate or insufflate an interior of a body lumen. The channels may include one or more coatings to be more lubricious.

Figure 2A:
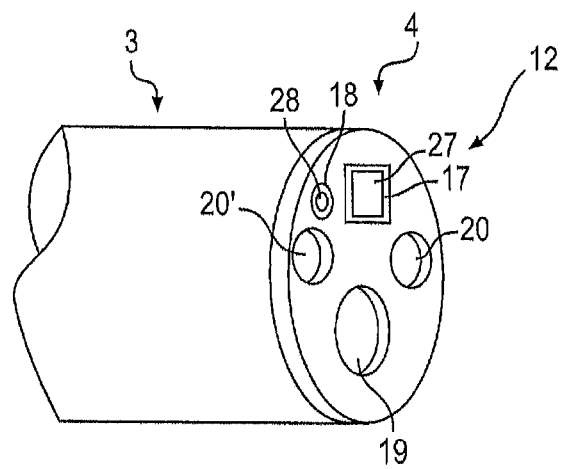
FIG. 2A illustrates a perspective view of a distal region of a medical device, according to an exemplary disclosed embodiment.
Figure 2B:
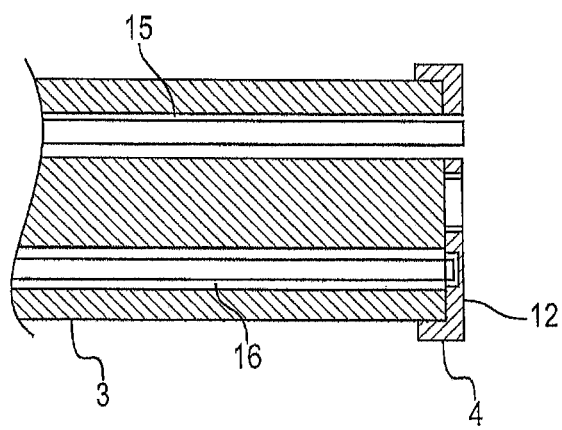
FIG. 2B illustrates a cross-sectional view of a distal region of a medical device, according to an exemplary disclosed embodiment.
Figure 3A:
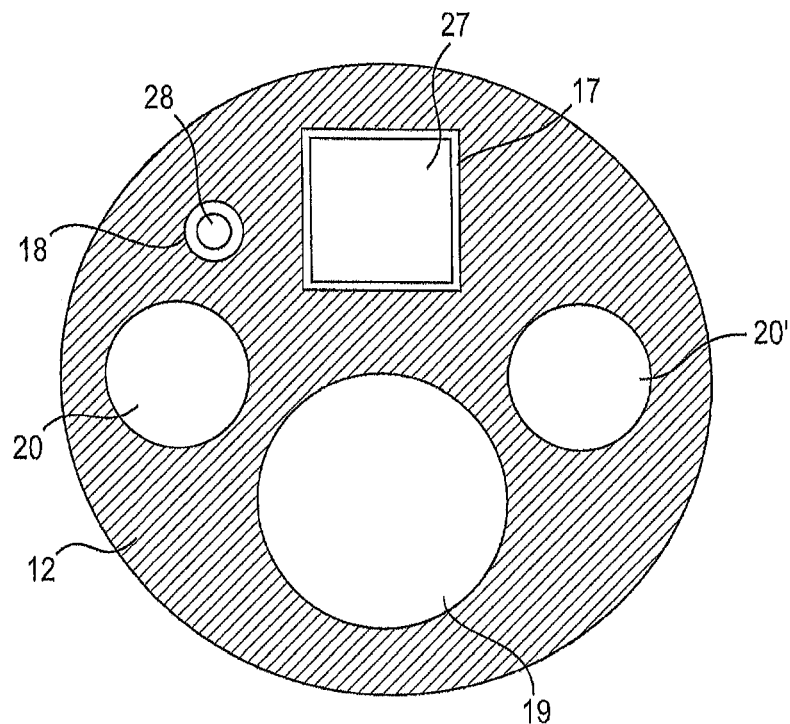
FIGS. 3A-3B illustrate end views of exemplary distal ends of a medical device, according to exemplary disclosed embodiments.
Figure 3B:
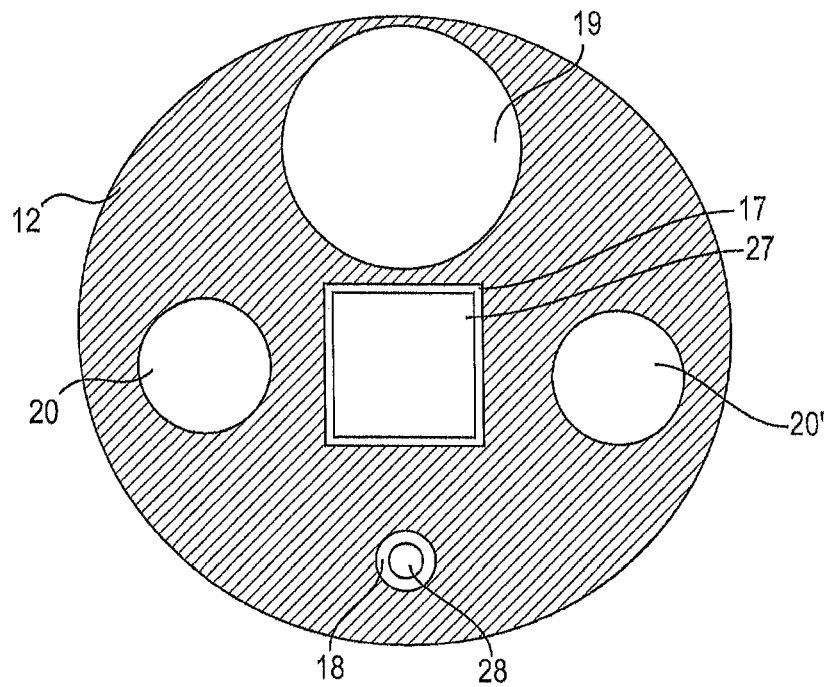

Distal tip 4 may be located at a distal region of elongate member 3. An exterior face 12 of distal tip 4 can define openings in communication with one or more channels 15, 16 in elongate member 3. These openings may fluidly connect channels 15, 16 in elongate member 3 to face 12 of medical device 1 and to regions exterior of medical device 1, as shown in FIGS. 2A-2B. For instance, an instrument passed through a working channel may exit a working opening 19 in distal tip 4 so that the instrument can protrude from medical device 1 to a work site. In another embodiment, the instrument may be configured as an end-effector attached at a distal region of medical device 1 and configured to pass through working opening 19.

The openings on face 12 of distal tip 4 may have any size, cross-sectional area, shape, and/or configuration. Further, while FIGS. 2A-3B depict two channels 15, 16 exiting or terminating in distal tip 4, distal tip 4 may include an exit or termination point for only one channel, or for more than two channels. The number, arrangement, or type of channels included in elongate member 3 and the number, arrangement, or type of openings in distal tip 4 depicted in the embodiments are exemplary. Medical device 1 may include any suitable number, type, or arrangement of channels or openings. Further, the ratio of channels in elongate member 3 to openings in distal tip 4 need not be one-to-one.

In some embodiments, distal tip 4 may be integral with a distal region of elongate member 3, while in other embodiments, distal tip 4 may be one or more parts separate from a distal region of elongate member 3. In such embodiments, distal tip 4 may be secured to a distal region of elongate member 3 by, for example, an interference fit, a snap fit, threads, adhesive bonding, lock and key fit, or any other suitable securing mechanism. Distal tip 4 may be a removable or replaceable distal tip and may be reusable or disposable. Multiple types and/or configurations of distal tip 4 may be available for interchangeable use with a distal region of elongate member 3.

Further, distal tip 4 may have any useful shape to aid with procedures, deliver light, and/or diffuse light. For example, distal tip 4 may be cylindrical, bulbous, hemispherical, concave, or may have angled surfaces. In some embodiments, distal tip 4 may have rounded or beveled edges to provide increased patient comfort and to reduce the risk of injury to the patient.

In the embodiments in FIGS. 2A-2B and 3A-3B, face 12 of distal tip 4 includes opening 19 for a working channel, two openings 20, 20' for irrigation, suction, and/or insufflation channels, an opening 18 for an illumination unit 28, and an imaging opening 17 for an imaging unit 27. In addition, illumination opening 18 and imaging opening 17 may include windows or lenses to cover and protect illumination unit 28 and imaging unit 27, respectively. Face 12 of distal tip 4 can include any type, number, and/or configuration of openings or units.

Units positioned in the openings of distal tip 4 may be adjacent to, flush with, or protruding from distal tip 4 and/or the channels in which they are oriented. Further, units may be moveable in any direction relative to distal tip 4. For instance, illumination unit 28 or imaging unit 27 may be moveable within openings 18 or 17, respectively, in order to aid with visualization and imaging. In other embodiments, the units in distal tip 4 may be stationary.

Distal tip 4 may encase various optical components. For example, such optical components can include image detectors, light sources, fiberoptics, light shields, filters, lenses, etc. In the embodiment shown in FIGS. 2A-2B and 3A-3B, medical device 1 may include illumination unit 28 to illuminate a field of view at the work site and imaging unit 27 to allow a surgeon to see the work site from outside the body and to remotely operate medical device 1 or instruments passed through working opening 19 to perform a desired diagnostic/therapeutic procedure at the work site. Imaging unit 27 may be configured to capture images and/or full-motion video images. Illumination unit 28 may be configured to illuminate internal body lumens and/or cavities of a patient.

Figure 4:
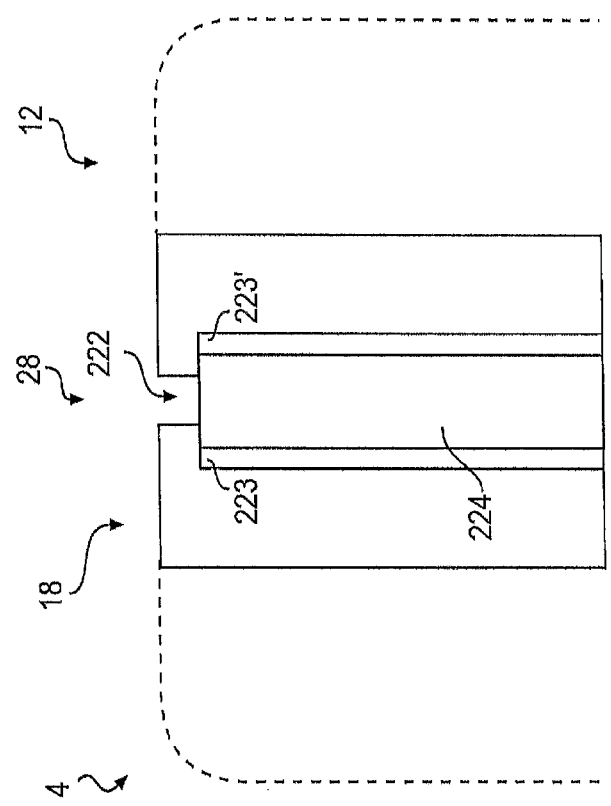
FIG. 4 illustrates a cross-sectional view of a distal region of a medical device, according to an exemplary disclosed embodiment.

Illumination unit 28 may be configured to provide both far-field and near-field illumination. FIG. 4 depicts a cross-section of an exemplary illumination unit 28 in illumination opening 18 located on distal tip 4. Illumination unit 28 may include one or more near-field diffusers 223, 223' and one or more far-field apertures 222. Far-field aperture 222 can be located adjacent to, on, or be formed as a part of face 12 of distal tip 4. Far-field aperture 222 may be circular, oval, rectangular, or any other suitable shape. Far-field aperture 222 may vary in cross-sectional shape or size from a distal end to a proximal end. For instance, far-field aperture 222 may be conical or bowl-shaped. In one embodiment, near-field diffuser 223 may extend longitudinally away from far-field aperture 222 in a proximal direction. In one embodiment, a single near-field diffuser 223 may substantially surround the periphery of far-field aperture 222. In some embodiments, a plurality of near-field diffusers 223, 223' may be located around the periphery of far-field aperture 222.

Distal tip 4 and near-field diffusers 223, 223' can be monolithically formed (e.g., formed in one piece), or distal tip 4 and near-field diffusers 223, 223' may be separate components. For instance, in some embodiments, distal tip 4 may itself be formed of a near-field diffuser 223 and may surround the periphery of far-field aperture 222, or may form the opening that forms far-field aperture 222. In one embodiment, illumination opening 18 on face 12 of distal tip 4 may define far-field aperture 222. When distal tip 4 acts as near-field diffuser 223, it can be formed, for example, with a plastic or glass material. In some embodiments, distal tip 4 may be formed with a transparent material and can be configured, for example, to filter or enhance certain wavelengths of light. The material used to form distal tip 4 can be selected based on the material's optical properties, such as its ability to transmit light of a particular wavelength(s). Distal tip 4 can be, for example, molded or post-processed to form optically transmissive regions. Distal tip 4 may be made of a translucent plastic or material by any suitable method, including, for example, injection molding, machining, or lithography. In one embodiment, distal tip 4 may be formed of an acrylic polymer filled with a diffuser, such as titanium dioxide. The acrylic material may create a scatter effect to light that enters distal tip 4. Scattering may be facilitated by any number of ways known in the art, including fillers, opaque materials, bubbles, diffusing or opaque coatings, surface treatments, or patterns. For example, one or more portions of distal tip 4 may include holes, pores, particulates, bubbles, or may be partially or substantially hollowed out, or may include any suitable configuration for affecting light transmission.

A light source 224 may be configured to direct light through near-field diffuser 223 and far-field aperture 222. Light source 224 can include, for instance, one or more optical fibers, one or more LEDs, or any other suitable light source or combination thereof. Light source 224 can be formed of quartz, glass, plastic, or any other suitable material. In one embodiment, a single light source, e.g., a single optical fiber or a single LED, can be configured to direct light through both near-field diffuser 223 and far-field aperture 222.

Light source 224 may be positioned in line with far-field aperture 222, and one or more portions of light source 224 may be substantially surrounded by near-field diffuser 223. Light source 224 may be adjacent to or placed in contact with near-field diffuser 223. In one embodiment, light source 224 may extend longitudinally away from far-field aperture 222 in a proximal direction. For example, light source 224 may extend from a proximal region through an illumination channel in elongate member 3 to illumination unit 28 in illumination opening 18 of distal tip 4. Light source 224 may be configured to direct light through both near-field diffuser 223 and far-field aperture 222, and me located distal to one or both of near-field diffuser 223 and far-field aperture 222.

Light source 224 may be recessed within distal tip 4 proximal to face 12. In other embodiments, light source 224 may be flush with face 12, or may protrude distally from face 12 of distal tip 4. Light source 224 may be moveable relative to distal tip 4, for example, axially or rotationally.

As light from light source 224 passes through near-field diffuser 223, light rays may be spread out at a large angle such that light is directed towards the periphery of the body lumen into which distal tip 4 may be inserted. Near-field diffuser 223 may be configured to spread the light from light source 224 that is discharged from illumination unit 28 to produce a softer light that reduces harsh glare, saturation and/or hard shadows. Thus, near-field images captured by imaging unit 27 may be softer and clearer. This can result in a uniform near-field illumination pattern.

The material and thickness of near-field diffuser 223 may affect the diffusing angle and uniformity of the illumination pattern produced by illumination unit 28. Near-field diffuser 223 can be formed of any suitable structure, material, or combination of materials for spreading light from light source 224, for example, ground glass, opal glass, grayed glass, and various white opaque plastics, such as titanium-filled acrylic and glass-filled polycarbonate. In some embodiments, distal tip 4 may be injection molded from any suitable, optically clear material that may be loaded with 1 to 15% titanium dioxide, and thus, the material of distal tip 4 may function as a diffuser.

Light from light source 224 entering far-field aperture 222 may not be diffused and may therefore be directed out of illumination unit 28 collinear with distal tip 4. Far-field aperture 222 may be configured to direct higher-intensity, concentrated light from illumination unit 28. Accordingly, light passing through far-field aperture 222 can form a centralized, compact illumination profile, allowing for a uniform far-field illumination pattern and improved down-lumen visualization.

The size of the aperture can determine the down-lumen spot size and the down-lumen visualization distance. The size of far-field aperture 222 can be smaller or larger than the tip of light source 224. In some embodiments, the aperture size can be variable. For instance, far-field aperture 222 may be operably coupled to proximal handle assembly 2 and configured so that a user may adjust the size of far-field aperture 222. In one embodiment, one or more illumination units 28 may be operably connected to one or more imaging units 27. In this embodiment, for instance, the size of aperture 222 may be automatically adjusted based on signals received and/or processed from imaging unit 27. In other embodiments, the size of far-field aperture 222 may be fixed. Far-field aperture 222 may also include a cover, filter, diffuser, or any other suitable structure to control far-field illumination.

The properties of far-field aperture 222 and near-field diffuser 223 can be tailored depending on the requirements of the type of medical device 1 used or the therapeutic or diagnostic procedure performed. Furthermore, distal tip 4 may include multiple light sources 224—either a bundle of optical fibers or an array of LEDs in a single illumination unit 28, or multiple illumination units 28 using single or multiple optical fibers or LEDs—to increase light intensity and/or to alter the illumination pattern.

In some embodiments, distal tip 4 may house components that are unique to distal tip 4 and do not extend through channels in elongate member 3, or that only partially extend through channels. For instance, illumination opening 18 in distal tip 4 may or may not fluidly connect with one or more corresponding channels extending through elongate member 3 and instead may terminate within a recess in distal tip 4. For example, while working opening 19 in distal tip 4 may fluidly connect with a working channel in elongate member 3, optical components may or may not extend through corresponding channels in elongate member 3, or may only partially extend through a channel. Imaging unit 27 and/or illumination unit 28 may or may not be entirely contained in openings 17 and 18, respectively, in distal tip 4.

In one embodiment, an optical component can extend within an opening of distal tip 4 such that a distal end portion of the optical component is encased within distal tip 4 and a proximal end portion of the component can extend out a proximal end of distal tip 4 and through a channel of elongate member 3. For example, optical components having a power line or signal line, such as light source 224 (FIG. 4) in illumination unit 28 or a component in imaging unit 27, can have a power line or signal line extending out of a proximal end of distal tip 4. Imaging unit 27 can be coupled to a proximal imaging controller (not shown) via conductors, such as electrical wires, passing through a channel of medical device 1, as described above. Thus, images of a body lumen can be captured by imaging unit 27 and processed by the imaging controller. The images can also be communicated to an eyepiece or display device (not shown). Imaging unit 27 may include a camera, lens, digital-imaging chip, or other image-receiving device, which may transmit signals using wire or cable within a channel of elongate member 3.

As alluded to above, medical device 1 may be coupled to a control module and may include imaging electronics configured to process and/or transfer signals received from imaging unit 27 to a display (not shown) for viewing by a user. The control module may also be operably connected to light source 224, such as a fiber optic source, halogen source, or LED source, configured to deliver light to illumination unit 28, and/or illumination electronics configured to process and/or transfer signals controlling illumination unit 28. One or more actuators or buttons may be disposed on the control module to control illumination unit 28 and/or imaging unit 27. Alternatively, the one or more actuators or buttons may be disposed on handle assembly 2 of medical device 1 for controlling illumination unit 28 or imaging unit 27.

In one embodiment, illumination unit 28 may be operably connected to handle assembly 2 and may provide a communication pathway between a control module and both imaging unit 27 and illumination unit 28. For example, a connector may provide electronic signaling pathways for imaging unit 27 to transmit image data to a control module, for a control module to transmit image control signals to imaging unit 27, and for a control module to control light delivered from light source 224 to illumination unit 28. It should be appreciated that in other embodiments, however, light source 224 may be housed in handle assembly 2, and illumination unit 28 may be operably connected to light source 224 within handle assembly 2. Light source 224 may then be operably coupled to a control module via a connector.

A connector may include any appropriate linkage configured to provide signaling capabilities and communication between a control module and both imaging unit 27 and illumination unit 28, such as, for example, one or more electrical wires, an electrical conduit, or other suitable connectors. A connector may also include a suitable structure configured to readily attach and detach from a control module, such as, for example, a detachable point-to-point adapter, a detachable splice, and a detachable multi-port adapter. The one or more electrical wires may extend from handle assembly 2, through a channel in elongate member 3, and connect to imaging unit 27 in imaging opening 17 at distal tip 4. Illumination unit 28 may also extend from handle assembly 2, through a channel in elongate member 3, and terminate in illumination opening 18 at distal tip 4.

A user may control light directed through light source 224 and illumination unit 28 jointly or independently of a control system to optimize visualization. One or more than one light source 224 and one or more than one imaging unit 28 may be centerplated on distal tip 4 and controlled by a user. Further, a user may independently control the characteristics of light using, for instance, controls located on handle assembly 2, or a control system (not shown) may control the characteristics of light. The characteristics may include intensity, wavelength, polarization, color, frequency, phase, or any other characteristic that can vary the level of illumination directed through light source 224 and/or illumination unit 28. For instance, light delivered from light source 224 and/or illumination unit 28 may be colored or white, filtered or unfiltered, pulsing or steady, intense or dull, e.g., and these characteristics may be constant or may change, for instance, automatically, in response to user control, or according to preset conditions.

Any aspect set forth in any embodiment may be used with any other embodiment set forth herein. Every device and apparatus set forth herein may be used in any suitable medical procedure, may be advanced through any suitable body lumen and body cavity, and may be used for treatment or observation of any suitable body portion. For example, the apparatuses and methods described herein may be used in any natural body lumen or tract, including those accessed orally, vaginally, or rectally.

The many features and advantages of the present disclosure are apparent from the detailed specification, and thus, it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

What is claimed is:

1. A device, comprising:
   a shaft, including:
      a distal end, and
      a passage extending through the shaft to the distal end; and
   a cap at the distal end of the shaft; and
   an illumination unit extending through the passage to the cap, wherein the illumination unit is configured to illuminate an area distal to the cap, and wherein the illumination unit includes:
      a light source configured to emit light,
      a diffuser configured to diffuse a first portion of light emitted by the light source, and emit the diffused first portion of light into the area distal to the cap,
      an aperture, wherein a second portion of light emitted by the light source is unobstructed as the second portion of light leaves the light source, enters the aperture, and exits the aperture into the area distal to the cap.

2. The device of claim 1, wherein a layer of material forming the aperture is light-transmissive.

3. The device of claim 2, wherein the layer of material forming the aperture is on an outer surface of the diffuser.

4. The device of claim 2, wherein the layer of material forming the aperture includes a flange portion surrounding a periphery of the aperture distal to a distal end of the light source.

5. The device of claim 1, wherein the diffuser is disposed between the cap and the light source.

6. The device of claim 1, wherein the diffuser surrounds and contacts an outer surface of a distal end of the light source.

7. The device of claim 1, wherein the second portion of light emitted from the aperture is at least one of more centralized, more concentrated, and higher-intensity than the first portion of light emitted from the diffuser.

8. A device, comprising:
   a shaft, including:
      a distal end, and
      a passage extending through the shaft to the distal end; and
   a cap at the distal end of the shaft;
   a light source configured to emit light for illuminating an area distal to the cap;
   a diffuser configured to diffuse a first portion of light emitted by the light source, and emit the diffused first portion of light into the area distal to the cap; and
   an aperture, wherein a second portion of light emitted by the light source is unobstructed as the second portion of light leaves the light source, enters the aperture, and exits the aperture into the area distal to the cap.

9. The device of claim 8, wherein the second portion of light emitted from the aperture is more centralized, relative to a central longitudinal axis of the shaft, than light emitted from the diffuser.

10. The device of claim 8, wherein the second portion of light emitted from the aperture has a higher intensity than light emitted from the diffuser.

11. The device of claim 8, wherein the second portion of light emitted from the aperture is more concentrated than light emitted from the diffuser.

12. The device of claim 8, wherein the diffuser is within the cap, and the diffuser surrounds and contacts an outer surface of a distal end of the light source.

13. The device of claim 8, wherein the aperture is located at a distalmost face of the cap.

14. A device, comprising:
   a shaft, including:
      a distal end, and
      a passage extending through the shaft to the distal end; and
   a cap at the distal end of the shaft;
   a light source configured to emit light beyond the cap;
   a first light-emitting portion configured to emit a first portion of light from the light source to a first area beyond the cap; and
   a second light-emitting portion configured to emit a second portion of light from the light source to a second area beyond the cap, wherein the second portion of light is different from the first portion of light in at least one of a degree of centralization, intensity, and concentration.

15. The device of claim 14, wherein the second portion of light has a higher intensity than the first portion of light.

16. The device of claim 14, wherein the second portion of light is more concentrated than the first portion of light.

17. The device of claim 14, wherein light rays of the second portion of light are more centralized than light rays of the first portion of light.

18. The device of claim 14, wherein the second area is distal to the first area.

19. The device of claim 14, wherein the second light-emitting portion includes a layer of material through which light travels before being emitted from the layer of material as the second portion of light.

20. The device of claim 14, wherein the layer of material forming the second light-emitting portion includes a flange portion surrounding a periphery of the second light-emitting portion distal to a distal end of the light source.

* * * * *